United States Patent
Nakagawa

(10) Patent No.: US 9,613,790 B2
(45) Date of Patent: Apr. 4, 2017

(54) ELECTRON SPECTROMETER AND MEASUREMENT METHOD

(71) Applicant: JEOL Ltd., Tokyo (JP)

(72) Inventor: Yasuhide Nakagawa, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/064,954

(22) Filed: Mar. 9, 2016

(65) Prior Publication Data

US 2016/0268119 A1 Sep. 15, 2016

(30) Foreign Application Priority Data

Mar. 12, 2015 (JP) ................. 2015-049438

(51) Int. Cl.
| | |
|---|---|
| *H01J 49/00* | (2006.01) |
| *H01J 49/48* | (2006.01) |
| *H01J 49/44* | (2006.01) |
| *H01J 37/22* | (2006.01) |
| *H01J 37/285* | (2006.01) |
| *G01N 23/227* | (2006.01) |

(52) U.S. Cl.
CPC .......... *H01J 49/48* (2013.01); *G01N 23/2273* (2013.01); *H01J 37/224* (2013.01); *H01J 37/285* (2013.01); *H01J 49/0004* (2013.01); *H01J 49/44* (2013.01); *H01J 2237/057* (2013.01); *H01J 2237/24485* (2013.01)

(58) Field of Classification Search
CPC ........ H01J 49/48; H01J 37/285; H01J 37/224; H01J 49/0004; H01J 49/44; H01J 2237/057; H01J 2237/24485; G01N 23/2273

USPC ................................................ 250/306, 307
See application file for complete search history.

(56) References Cited

FOREIGN PATENT DOCUMENTS

| | | | |
|---|---|---|---|
| EP | 0246841 A2 | 11/1987 | |
| GB | EP 0246841 A2 * | 11/1987 | ............ H01J 37/252 |
| JP | 2011247870 A * | 12/2011 | |
| SE | WO 2013133739 A1 * | 9/2013 | .............. H01J 37/05 |
| WO | 2013133739 A1 | 9/2013 | |

OTHER PUBLICATIONS

Extended European Search Report re EP 16159727.3 dated Jul. 12, 2016.

* cited by examiner

*Primary Examiner* — Michael Maskell
(74) *Attorney, Agent, or Firm* — The Webb Law Firm

(57) ABSTRACT

An electron spectrometer includes: an energy analyzer section that energy-analyzes electrons emitted from a specimen; a micro-channel plate that amplifies the electrons analyzed by the energy analyzer section; a fluorescent screen that converts the electrons amplified by the micro-channel plate into light; a camera that photographs the fluorescent screen; and an effective range calculation section that calculates an effective range of the fluorescent screen within a camera image photographed by the camera, the effective range calculation section performing a process that acquires a plurality of the camera images photographed while causing the energy analyzer section to analyze the electrons with a different center energy, a process that converts the plurality of camera images respectively into a plurality of spectra, and a process that calculates the effective range of the fluorescent screen within the camera image based on the plurality of spectra.

8 Claims, 4 Drawing Sheets

ELECTRON SPECTROMETER AND MEASUREMENT METHOD

Japanese Patent Application No. 2015-049438, filed on Mar. 12, 2015, is hereby incorporated by reference in its entirety.

BACKGROUND OF THE INVENTION

The present invention relates to an electron spectrometer and a measurement method.

An electron spectrometer such as an X-ray photoelectron spectroscope (XPS) and an Auger electron microscope (AES) is known as a device that is used to analyze the surface of a solid.

For example, JP-A-2011-247870 discloses a detector that includes a micro-channel plate (MCP), a fluorescent screen, and a CCD camera as a detector that is provided to such an electron spectrometer. The micro-channel plate two-dimensionally detects the incident electrons, multiplies the electrons on a channel basis, and outputs the multiplied electrons to the fluorescent screen. The fluorescent screen receives the electrons that have been multiplied by the micro-channel plate on a channel basis, and output from the micro-channel plate, and produces visible light having a brightness corresponding to the number of electrons that have reached it per unit time. The CCD camera photographs a visible light image formed by the fluorescent screen.

The image of the fluorescent screen photographed by the CCD camera changes depending on the magnification of the camera lens, the positional relationship between the camera and the fluorescent screen, and the like. It is normally possible to absorb such a change by setting the size of the rectangular camera image (e.g., Video Graphics Array (VGA) and Extended Graphics Array (XGA)) to be larger than the fluorescent screen. However, it is difficult to accurately calculate the geometric position of the fluorescent screen within the camera image. Moreover, since the edge of the fluorescent screen does not necessarily accurately coincide with the diameter of the micro-channel plate, it is difficult to accurately determine the effective range of the fluorescent screen with the naked eye.

SUMMARY

The invention may provide an electron spectrometer that can accurately calculate the effective range of the fluorescent screen within the camera image, and a measurement method that can accurately calculate the effective range of the fluorescent screen within the camera image.

According to a first aspect of the invention, there is provided an electron spectrometer including:

an energy analyzer section that energy-analyzes electrons emitted from a specimen;

a micro-channel plate that amplifies the electrons analyzed by the energy analyzer section;

a fluorescent screen that converts the electrons amplified by the micro-channel plate into light;

a camera that photographs the fluorescent screen; and an effective range calculation section that calculates an effective range of the fluorescent screen within a camera image photographed by the camera, the effective range calculation section performing a process that acquires a plurality of the camera images photographed while causing the energy analyzer section to analyze the electrons with a different center energy, a process that converts the plurality of camera images respectively into a plurality of spectra, and a process that calculates the effective range of the fluorescent screen within the camera image based on the plurality of spectra.

According to a second aspect of the invention, there is provided a measurement method that is implemented by an electron spectrometer that includes an energy analyzer section that energy-analyzes electrons emitted from a specimen, a micro-channel plate that amplifies the electrons analyzed by the energy analyzer section, a fluorescent screen that converts the electrons amplified by the micro-channel plate into light, and a camera that photographs the fluorescent screen, the measurement method calculating an effective range of the fluorescent screen within a camera image photographed by the camera, the measurement method including:

a step that acquires a plurality of the camera images photographed while causing the energy analyzer section to analyze the electrons with a different center energy;

a step that converts the plurality of camera images respectively into a plurality of spectra; and a step that calculates the effective range of the fluorescent screen within the camera image based on the plurality of spectra.

Figure 1:
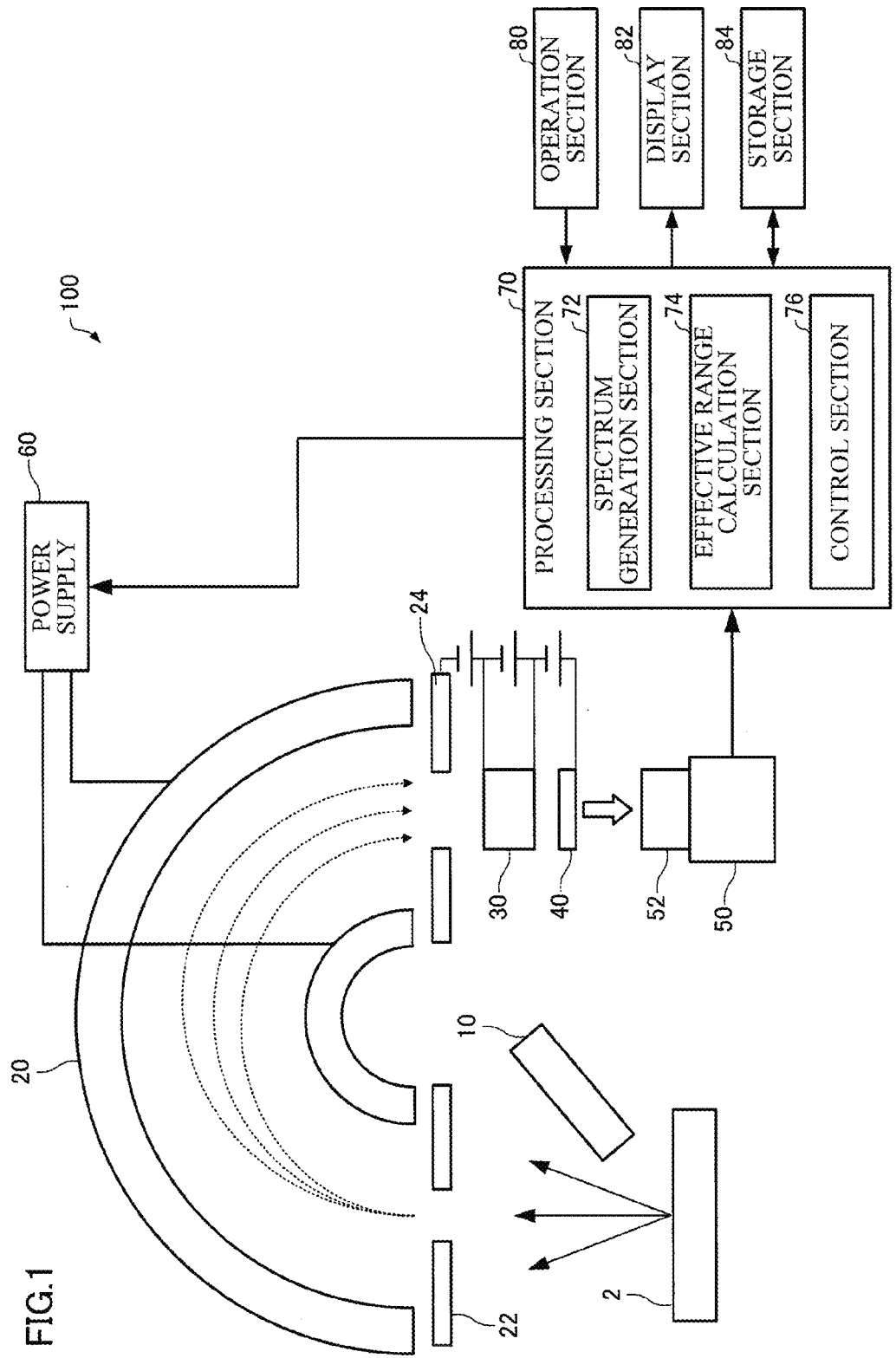
FIG. 1 schematically illustrates the configuration of an electron spectrometer according to one embodiment of the invention.

DETAILED DESCRIPTION OF THE EMBODIMENT (1) According to one embodiment of the invention, an electron spectrometer includes:

an energy analyzer section that energy-analyzes electrons emitted from a specimen;

a micro-channel plate that amplifies the electrons analyzed by the energy analyzer section;

a fluorescent screen that converts the electrons amplified by the micro-channel plate into light;

a camera that photographs the fluorescent screen; and an effective range calculation section that calculates an effective range of the fluorescent screen within a camera image photographed by the camera, the effective range calculation section performing a process that acquires a plurality of the camera images photographed while causing the energy analyzer section to analyze the electrons with a different center energy, a process that converts the plurality of camera images respectively into a plurality of spectra, and a process that calculates the effective range of the fluorescent screen within the camera image based on the plurality of spectra.

Since the electron spectrometer is configured so that the effective range calculation section performs the process that acquires a plurality of camera images photographed while causing the energy analyzer section to analyze the electrons with a different center energy, the process that converts the plurality of camera images respectively into a plurality of spectra, and the process that calculates the effective range of the fluorescent screen within the camera image based on the plurality of spectra, it is possible to accurately calculate the effective range of the fluorescent screen within the camera image as compared with the case of geometrically calculating the effective range of the fluorescent screen from the positional relationship between the camera and the fluorescent screen, for example.

(2) In the electron spectrometer, in the process that calculates the effective range of the fluorescent screen, the effective range calculation section may determine the maximum brightness position within the camera image from each of the plurality of spectra, and then calculate the effective range of the fluorescent screen based on the center energy and the maximum brightness position.

(3) In the electron spectrometer, in the process that calculates the effective range of the fluorescent screen, the effective range calculation section may draw a graph in which the center energy and the maximum brightness position are respectively plotted along a first axis and a second axis with respect to each of the plurality of spectra, and then calculate the effective range of the fluorescent screen from the graph.

(4) In the electron spectrometer, the effective range calculation section may perform a process that calculates an energy axis within the camera image based on the center energy and the maximum brightness position.

The electron spectrometer can thus accurately calculate the energy axis within the camera image as compared with the case of geometrically calculating the energy axis within the camera image from the positional relationship between the camera and the fluorescent screen, for example.

(5) According to one embodiment of the invention, a measurement method is implemented by an electron spectrometer that includes an energy analyzer section that energy-analyzes electrons emitted from a specimen, a micro-channel plate that amplifies the electrons analyzed by the energy analyzer section, a fluorescent screen that converts the electrons amplified by the micro-channel plate into light, and a camera that photographs the fluorescent screen, the measurement method calculating an effective range of the fluorescent screen within a camera image photographed by the camera, the measurement method including:

a step that acquires a plurality of the camera images photographed while causing the energy analyzer section to analyze the electrons with a different center energy;

a step that converts the plurality of camera images respectively into a plurality of spectra; and a step that calculates the effective range of the fluorescent screen within the camera image based on the plurality of spectra.

The measurement method can thus accurately calculate the effective range of the fluorescent screen within the camera image as compared with the case of geometrically calculating the effective range of the fluorescent screen from the positional relationship between the camera and the fluorescent screen, for example.

(6) In the measurement method, the step that calculates the effective range of the fluorescent screen may include determining a maximum brightness position within the camera image from each of the plurality of spectra, and calculating the effective range of the fluorescent screen based on the center energy and the maximum brightness position.

(7) In the measurement method, the step that calculates the effective range of the fluorescent screen may include drawing a graph in which the center energy and the maximum brightness position are respectively plotted along a first axis and a second axis with respect to each of the plurality of spectra, and calculating the effective range of the fluorescent screen from the graph.

(8) The measurement method may further include a step that calculates an energy axis within the camera image based on the center energy and the maximum brightness position.

The measurement method can thus accurately calculate the energy axis within the camera image as compared with the case of geometrically calculating the energy axis within the camera image from the positional relationship between the camera and the fluorescent screen, for example.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. Electron Spectrometer

An electron spectrometer according to one embodiment of the invention is described below with reference to the drawings. FIG. 1 schematically illustrates the configuration of an electron spectrometer 100 according to one embodiment of the invention. An example in which the electron spectrometer 100 is an X-ray photoelectron spectroscope (spectrometer) that energy-analyzes electrons emitted from a specimen upon application of X-rays is described below.

As illustrated in FIG. 1, the electron spectrometer 100 includes an X-ray source 10, an energy analyzer section 20, a micro-channel plate 30, a fluorescent screen 40, a camera 50, a power supply 60, a processing section 70, an operation section 80, a display section 82, and a storage section 84.

The X-ray source 10 applies X-rays to a specimen 2. When X-rays have been applied to the specimen 2, electrons (photoelectrons) are emitted from the specimen 2 due to a photoelectric effect.

An entrance slit 22 may be disposed to precede the energy analyzer section 20. The entrance slit 22 limits the photoelectrons that enter the energy analyzer section 20.

The energy analyzer section 20 energy-analyzes the photoelectrons emitted from the specimen 2. The energy analyzer section 20 extracts electrons having a specific energy through photoelectron energy discrimination (selection).

The energy analyzer section 20 is an electrostatic hemispherical analyzer, for example. The electrostatic hemispherical analyzer is configured so that a voltage is applied between an outer sphere and an inner sphere to form a spherically symmetric electric field, for example. When electrons having an equal energy are caused to be incident at various angles from one point within the spherically symmetric electric field, the electrons rotate by 180°, and converge on an approximately identical point. When electrons having a different energy are caused to be incident on the spherically symmetric electric field, the electrons converge on another point. Therefore, it is possible to implement energy analysis by causing electrons having a certain energy spread to be incident on such a field. Specifically, the electrostatic hemispherical analyzer is configured so that the position of an electron detected in the exit plane corresponds to the energy (kinetic energy) of the electron.

The electrons that have been analyzed by the electrostatic hemispherical analyzer are applied to the micro-channel plate 30 so as to have a dispersion width corresponding to the pass energy (i.e., the voltage applied between the outer sphere and the inner sphere) of the analyzer with respect to the center energy (i.e., the center energy of the energy analyzer section 20 (hereinafter may be referred to as "center energy Ec")) of the analyzer. For example, the center of the energy spread of the electrons that enter the micro-channel plate 30 corresponds to the center energy Ec of the energy analyzer section 20.

The energy analyzer section 20 is configured so that the center energy Ec can be changed. For example, the center energy Ec can be changed by changing the voltage applied between the outer sphere and the inner sphere of the electrostatic hemispherical analyzer. For example, it is possible to obtain a plurality of spectra that differ in the center energy Ec by continuously photographing a photoelectron image while changing (scanning) the center energy Ec of the energy analyzer section 20. For example, when the energy spread (i.e., the energy spread of the electrons in the exit plane) analyzed by the energy analyzer section 20 is 0.8 eV, it is possible to obtain a spectrum within an energy range of 0 eV to 1.5 KeV by changing (scanning) the center energy Ec.

The electrons extracted by the energy analyzer section 20 enter the micro-channel plate 30 after being accelerated by an acceleration lens 24, for example.

The micro-channel plate 30 two-dimensionally detects the incident electrons, and multiplies the electrons on a channel basis. It is desirable that the channel resolution of the micro-channel plate 30 be higher than the resolution of the camera 50 with respect to the projection image (photoelectron image) projected onto the fluorescent screen 40. Note that it suffices that the channel resolution of the micro-channel plate 30 be higher than the number of channels required for the spectrum.

The fluorescent screen 40 converts the electrons amplified (multiplied) by the micro-channel plate 30 into light. When the electrons multiplied by the micro-channel plate 30 have been applied to the fluorescent screen 40, the fluorescent screen 40 produces visible light having a brightness corresponding to the number of electrons that have reached it per unit time.

The fluorescent screen 40 includes a transparent substrate, and a fluorescent material that is provided on the transparent substrate, for example. Since the transparent substrate allows visible light to pass through, the camera 50 can photograph the visible light from the back side (i.e., the side of the transparent substrate) of the fluorescent screen 40. It is desirable that the response speed of the fluorescent material be 1 ms or less (i.e., shorter than the spectrum integration time). The fluorescent screen 40 may be formed by a single-channel plate, and the electrons multiplied by the micro-channel plate 30 may be input as an electrical signal to implement pulse-count measurement.

A predetermined voltage is applied between the acceleration lens 24 and the micro-channel plate 30 and between the micro-channel plate 30 and the fluorescent screen 40 in order to guide the electrons analyzed by the energy analyzer section 20.

The camera 50 photographs the fluorescent screen 40. The camera 50 is a digital camera such as a charge coupled device (CCD) camera or a complementary metal oxide semiconductor (CMOS) camera, for example. The number of pixels of the camera 50 is equal to or larger than the number of channels required for the spectrum. A camera lens 52 is provided to precede the camera 50, and the camera 50 photographs the projection image projected onto the fluorescent screen 40 through the camera lens 52.

The power supply 60 applies a voltage between the outer sphere and the inner sphere of the energy analyzer section 20 (electrostatic hemispherical analyzer). The power supply 60 applies a voltage between the outer sphere and the inner sphere based on a control signal that is generated by a control section 76 (described later).

The electron spectrometer 100 is configured so that electrons emitted from the specimen 2 due to a photoelectric effect as a result of causing the X-ray source 10 to apply X-rays to the specimen 2 are analyzed by the energy analyzer section 20 in terms of energy, and applied to the micro-channel plate 30 so as to have a dispersion width corresponding to the pass energy of the energy analyzer section 20 with respect to the center energy Ec of the energy analyzer section 20. The fluorescent screen 40 converts the electrons multiplied by the micro-channel plate 30 into light, and a photoelectron image is projected onto the fluorescent screen 40. The photoelectron image projected onto the fluorescent screen 40 is photographed by the camera 50, and transmitted to the processing section 70.

The processing section 70 performs various processes according to this embodiment based on a program (data) stored in the storage section 84. The storage section 84 may store a program that causes a computer to function as each section of the processing section 70.

The processing section 70 performs a process that converts a camera image into a spectrum, a process that calculates the effective range of the fluorescent screen within the camera image, a process that calculates the energy axis within the camera image, and the like. The function of the processing section 70 may be implemented by hardware such as a processor (e.g., CPU or DSP) or an ASIC (e.g., gate array), or a program. The processing section 70 includes a spectrum generation section 72, an effective range calculation section 74, and the control section 76.

The spectrum generation section 72 converts a camera image obtained by photographing the photoelectron image into a spectrum. The spectrum generation section 72 generates the spectrum by integrating brightness information about the camera image in the direction perpendicular to the energy dispersion direction. The spectrum generated by the spectrum generation section 72 is displayed on the display section 82, for example.

The effective range calculation section 74 performs a process that calculates the effective range of the fluorescent screen within the camera image.

Figure 2:
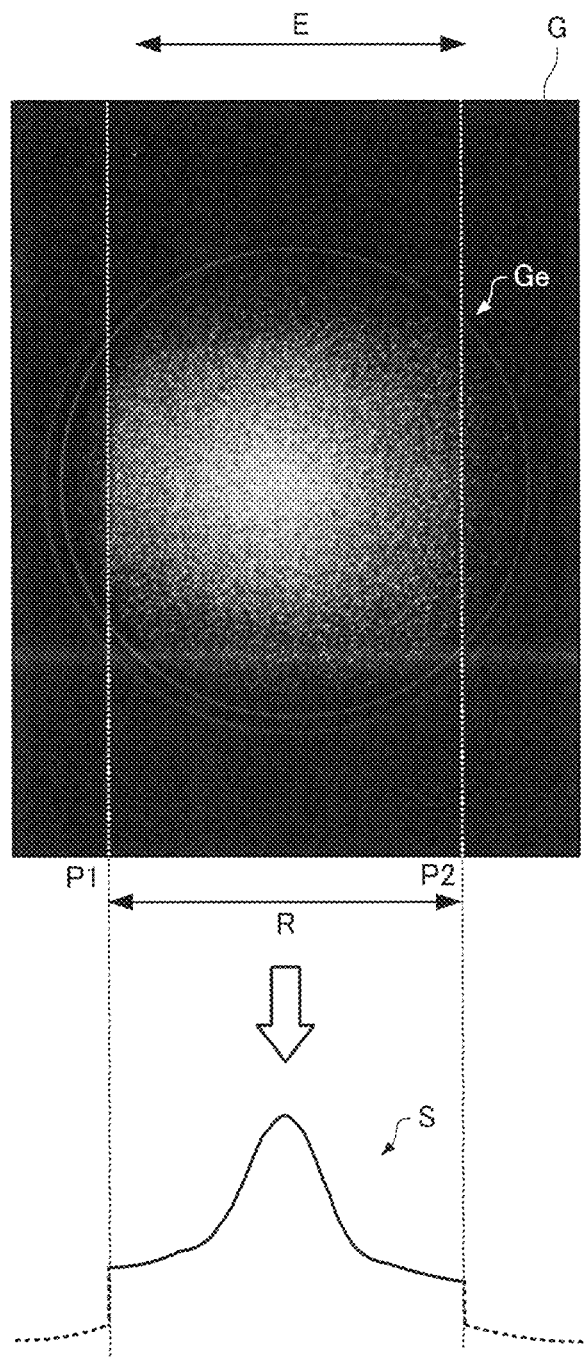
FIG. 2 illustrates an example of a camera image.

The effective range of the fluorescent screen within the camera image is described below. FIG. 2 illustrates an example of a camera image G.

For example, the camera image G has a resolution of 640×480 pixels. In the example illustrated in FIG. 2, the energy dispersion direction E is a direction parallel to the short side of the camera image G. A photoelectron image Ge projected onto the fluorescent screen 40 is captured within the camera image G. A spectrum S is obtained by integrating the brightness information about the camera image G in the direction perpendicular to the energy dispersion direction E of the photoelectron image Ge.

In the example illustrated in FIG. 2, the range within the camera image G in which the brightness information about the photoelectron image Ge is effective (i.e., the range within the camera image G in which the energy distribution obtained by the analysis performed by the energy analyzer section 20 is reflected) is a range R between a position P1 of one end of the photoelectron image Ge and a position P2 of the other end of the photoelectron image Ge in the energy dispersion direction E. The range within the camera image G in which the brightness information about the photoelectron image Ge is effective (i.e., the range R in the example illustrated in FIG. 2) is referred to as the effective range of the fluorescent screen within the camera image (hereinafter may be referred to as "the effective range of the fluorescent screen").

The effective range calculation section 74 performs a process that acquires a plurality of camera images obtained while causing the energy analyzer section 20 to analyze the electrons emitted from the specimen 2 with a different center energy Ec, a process that converts the plurality of camera images respectively into a plurality of spectra, and a process that calculates the effective range R of the fluorescent screen based on the plurality of spectra.

When the effective range calculation section 74 performs the process that calculates the effective range R of the fluorescent screen, the effective range calculation section 74 determines the maximum brightness position within the camera image from each spectrum, and calculates the effective range R of the fluorescent screen based on the center energy Ec and the maximum brightness position. For example, the effective range calculation section 74 draws a graph in which the center energy Ec (first axis) and the maximum brightness position (second axis) are plotted with respect to each spectrum, and calculates the effective range R of the fluorescent screen from the graph.

The effective range calculation section 74 also performs a process that calculates the energy axis (pixel/eV) within the camera image based on the plurality of spectra.

The control section 76 performs a process that generates the control signal that controls the energy analyzer section 20. The control section 76 generates the control signal based on the center energy Ec when the center energy Ec has been set, and outputs the control signal to the power supply 60. For example, the user may set the center energy Ec through the operation section 80. When a process that photographs a plurality of camera images is performed automatically (as described later), the control section 76 may read information about the reference center energy Ec (i.e., the center energy Ec when the scan is started) and information about the amount of change in the center energy Ec that corresponds to one step (that are stored in advance in the storage section 84) to set the center energy Ec. The power supply 60 applies a voltage between the outer sphere and the inner sphere of the electrostatic hemispherical analyzer based on the control signal.

The operation section 80 allows the user to input operation information, and outputs the operation information input by the user to the processing section 70. The function of the operation section 80 may be implemented by hardware such as a keyboard, a mouse, a button, a touch panel, or a touch pad.

The display section 82 displays an image generated by the processing section 70. The function of the display section 82 may be implemented by an LCD, a CRT, a touch panel (that also functions as the operation section 80), or the like.

The storage section 84 stores a program that causes a computer to function as each section of the processing section 70 as well as various types of data, and serves as a work area for the processing section 70. The function of the storage section 84 may be implemented by a hard disk, a RAM, or the like.

2. Measurement Method that Measures Effective Range of Fluorescent Screen within Camera Image A measurement method according to one embodiment of the invention that measures the effective range of the fluorescent screen within the camera image is described below.

Figure 3:
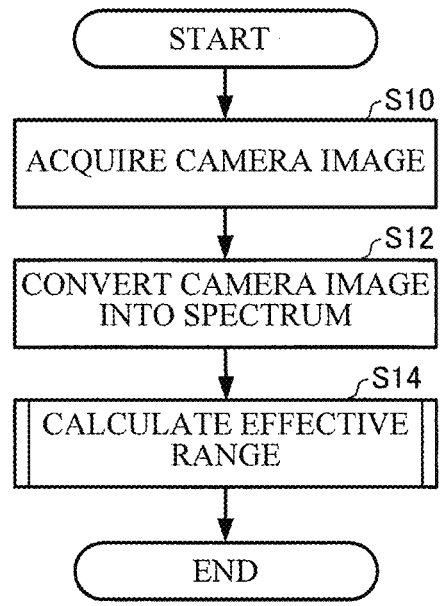
FIG. 3 is a flowchart illustrating an example of a measurement method according to one embodiment of the invention.

FIG. 3 is a flowchart illustrating an example of the measurement method according to one embodiment of the invention that measures the effective range of the fluorescent screen within the camera image. The electron spectrometer 100 is configured so that the effective range calculation section 74 performs the process that calculates the effective range of the fluorescent screen within the camera image.

Specifically, the effective range calculation section 74 acquires a plurality of camera images photographed while changing the center energy Ec of the energy analyzer section 20 (i.e., while causing the energy analyzer section 20 to analyze the electrons with a different center energy Ec) (step S10).

A plurality of camera images are photographed as described below.

A reference specimen for which a steep peak (e.g., $Ag3d_{5/2}$ photoelectron peak) is measured is used for the measurement. The center energy Ec of the energy analyzer section 20 is set so that the peak is situated at one end that is sufficiently away from the effective range of the fluorescent screen 40.

The photoelectron image projected onto the fluorescent screen 40 is then photographed by the camera 50. The photographed camera image is stored in the storage section 84.

The center energy Ec of the energy analyzer section 20 is then changed by one step. The step by which the center energy Ec is changed is set so that the moving distance on the micro-channel plate 30 when the center energy Ec is changed by one step is sufficiently smaller than the diameter of the micro-channel plate 30.

The photoelectron image projected onto the fluorescent screen 40 when the center energy Ec is changed by one step is then photographed by the camera 50. The photographed camera image is stored in the storage section 84.

A plurality of camera images photographed with a different center energy Ec are stored in the storage section 84 by repeating the above process. Specifically, a plurality of camera images photographed with a different center energy Ec are stored in the storage section 84 by continuously photographing the photoelectron image while changing (scanning) the center energy Ec of the energy analyzer section 20. The camera image is repeatedly photographed until the peak position moves across the effective range of the fluorescent screen and is situated on the other end that is sufficiently away from the effective range of the fluorescent screen.

A plurality of camera images can be photographed by the above process. Note that the control section 76 may perform the process that photographs a plurality of camera images. Specifically, the control section 76 may automatically perform the process that photographs a plurality of camera images.

Note that it is desirable to adjust the position and the magnification of the camera lens 52 and the camera 50 (i.e., adjust the focus of the camera 50) before the above process is performed so that the photoelectron image projected onto the fluorescent screen 40 is situated approximately at the center of the camera image (see FIG. 2, for example).

The effective range calculation section 74 reads a plurality of camera images stored in the storage section 84 to acquire a plurality of camera images photographed while changing the center energy Ec of the energy analyzer section 20.

The effective range calculation section 74 converts the plurality of camera images thus acquired respectively into a plurality of spectra (step S12).

The effective range calculation section 74 generates each spectrum by integrating the brightness information about the camera image in the direction perpendicular to the energy dispersion direction E (see FIG. 2).

The effective range calculation section 74 then calculates the effective range of the fluorescent screen within the camera image based on the plurality of spectra obtained by converting the plurality of camera images (step S14).

Figure 4:
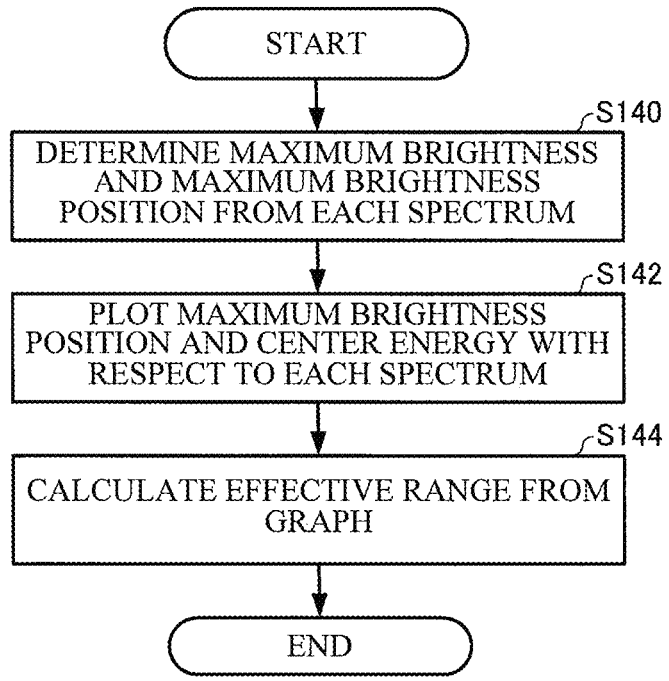
FIG. 4 is a flowchart illustrating an example of an effective range calculation process.

FIG. 4 is a flowchart illustrating an example of the effective range calculation process (step S14) performed by the effective range calculation section 74.

The effective range calculation section 74 determines the maximum brightness value within the camera image and the position within the camera image that corresponds to the maximum brightness value (hereinafter may be referred to as "maximum brightness position") from each spectrum (step S140).

Figure 5:
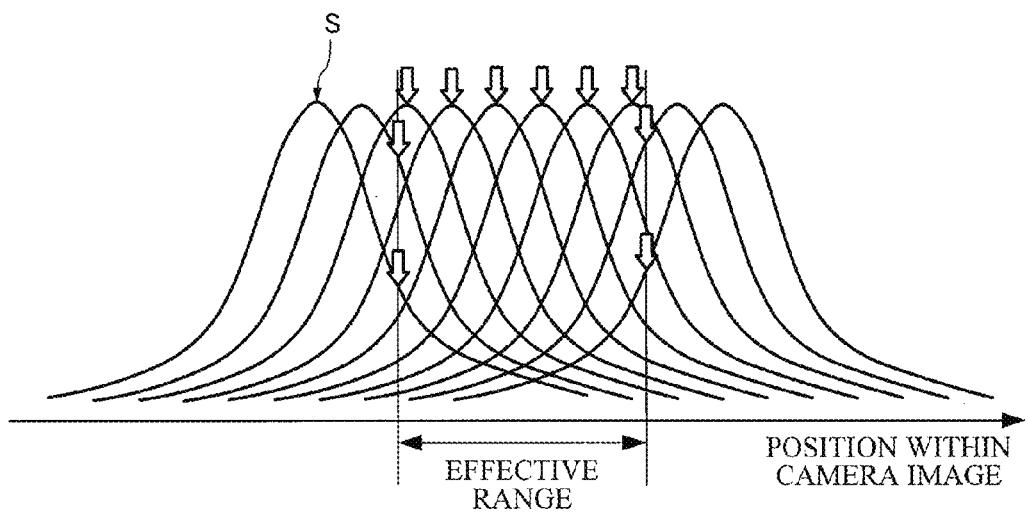
FIG. 5 schematically illustrates a plurality of spectra.

FIG. 5 schematically illustrates a plurality of spectra obtained by the step S12.

As illustrated in FIG. 5 in which the horizontal axis indicates the position (pixels) within the camera image and the vertical axis indicates the brightness (bits) of the image, the maximum brightness position (peak position) of each spectrum S obtained by the step S12 is the position indicated by the arrow in FIG. 5. Note that the maximum brightness position refers to the position within the camera image in the energy dispersion direction E.

The plurality of spectra obtained by the step S12 differ from each other as to the peak position (i.e., the maximum brightness position indicated by the arrow in FIG. 5) within the camera image. When the maximum brightness position of the spectrum S is not included within the effective range of the fluorescent screen, the lower-limit position or the upper-limit position of the effective range is determined to be the maximum brightness position.

The effective range calculation section 74 then draws a graph in which the center energy Ec (horizontal axis (first axis)) and the maximum brightness position (vertical axis (second axis)) are plotted with respect to each spectrum S (step S142). The effective range calculation section 74 calculates the effective range of the fluorescent screen from the graph (step S144).

Figure 6:
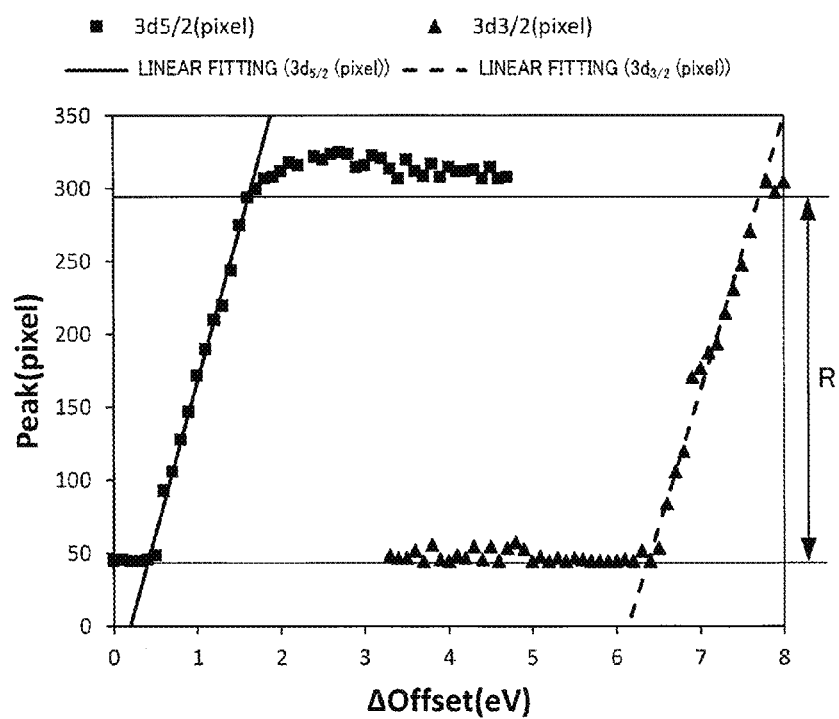
FIG. 6 illustrates a graph in which the center energy (horizontal axis) and the maximum brightness position (vertical axis) are plotted with respect to each spectrum.

FIG. 6 illustrates a graph in which the center energy Ec (horizontal axis) and the maximum brightness position (vertical axis) are plotted with respect to each spectrum S.

FIG. 6 illustrates the results obtained by plotting the center energy Ec and the maximum brightness position that corresponds to the $Ag3d_{5/2}$ photoelectron peak with respect to each spectrum S, and the results obtained by plotting the center energy Ec and the maximum brightness position that corresponds to the $Ag3d_{3/2}$ photoelectron peak with respect to each spectrum S. Note that the horizontal axis (deltaOffset) of the graph illustrated in FIG. 6 refers to the difference from the reference center energy Ec (i.e., the center energy Ec when the scan is started) of the energy analyzer section 20.

The effective range calculation section 74 performs a linear fitting process on the linear part in the graph illustrated in FIG. 6, and determines the resulting part to be the effective range R of the fluorescent screen. In the example illustrated in FIG. 6, the effective range R of the fluorescent screen within the camera image is the pixel range from 46 to 294. The effective range calculation section 74 determines the slope (pixel/eV) obtained by the linear fitting process to be the energy axis within the camera image.

According to the graph illustrated in FIG. 6, the effective range of the fluorescent screen and the energy axis within the camera image can be more accurately calculated by simultaneously acquiring the $Ag3d_{5/2}$ photoelectron peak and the $Ag3d_{3/2}$ photoelectron peak, and calculating the effective range of the fluorescent screen and the energy axis within the camera image. In the example illustrated in FIG. 6, the linear fitting result for the $Ag3d_{5/2}$ photoelectron peak is Y=208.6014X-41.69814, and the energy axis within the camera image is 208.6014 pixels/eV. The linear fitting result for the $Ag3d_{3/2}$ photoelectron peak is Y=187.14286X-1148.15385, and the energy axis within the camera image is 187.14286 pixels/eV.

The effective range calculation section 74 calculates the effective range of the fluorescent screen within the camera image and the energy axis within the camera image by using the above calculation method.

The effective range of the fluorescent screen within the camera image can be calculated by the above steps.

Although the above embodiments have been described taking an example in which the effective range calculation section 74 sequentially acquires and stores a plurality of camera images while changing the center energy Ec, and converts each camera image into a spectrum, the effective range calculation section 74 may repeat a process that immediately converts a camera image acquired using a certain center energy Ec into a spectrum, acquires a camera image while changing the center energy Ec, and converts each camera image into a spectrum.

The electron spectrometer 100 has the following features, for example.

The electron spectrometer 100 is configured so that the effective range calculation section 74 performs the process that acquires a plurality of camera images photographed while causing the energy analyzer section 20 to analyze electrons with a different center energy Ec, the process that converts the plurality of camera images respectively into a plurality of spectra, and the process that calculates the effective range of the fluorescent screen within the camera image based on the plurality of spectra. Therefore, the electron spectrometer 100 can accurately calculate the effective range of the fluorescent screen within the camera image as compared with the case of geometrically calculating the effective range of the fluorescent screen from the positional relationship between the camera and the fluorescent screen, for example. The electron spectrometer 100 can thus determine the effective range of the fluorescent screen independently of an individual geometric variation in the device.

Since the electron spectrometer 100 is configured so that the effective range calculation section 74 calculates the energy axis within the camera image based on the center energy Ec and the maximum brightness position of each spectrum, the electron spectrometer 100 can accurately calculate the energy axis within the camera image as compared with the case of geometrically calculating the energy axis within the camera image from the positional relationship between the camera and the fluorescent screen, for example. The electron spectrometer 100 can thus calibrate the energy axis within the camera image independently of an individual geometric variation in the device.

The measurement method according to the above embodiments includes a step (step S10) that acquires a plurality of camera images photographed while causing the energy analyzer section 20 to analyze electrons with a different center energy Ec, a step (step S12) that converts the plurality of camera images respectively into a plurality of spectra, and a step (step S14) that calculates the effective range of the fluorescent screen within the camera image based on the plurality of spectra. Therefore, it is possible to accurately calculate the effective range of the fluorescent screen within the camera image as compared with the case of geometrically calculating the effective range of the fluorescent screen from the positional relationship between the camera and the fluorescent screen, for example (see above).

The measurement method according to the above embodiments further includes a step that calculates the energy axis within the camera image based on the center energy Ec and the maximum brightness position of each spectrum. This makes it possible to accurately calculate the energy axis within the camera image as compared with the case of geometrically calculating the energy axis within the camera image from the positional relationship between the camera and the fluorescent screen, for example (see above).

The invention is not limited to the above embodiments. Various modifications and variations may be made of the above embodiments without departing from the scope of the invention.

Although the above embodiments have been described taking an example in which the electron spectrometer 100 is an X-ray photoelectron spectroscope that energy-analyzes electrons emitted from a substance upon application of X-rays, the electron spectrometer according to the invention may be a photoelectron spectroscope that energy-analyzes electrons emitted from a substance upon application of light (e.g., UV rays) other than X-rays. The electron spectrometer according to the invention may be an Auger electron microscope that energy-analyzes Auger electrons emitted from a substance upon application of electron beams.

The invention includes various other configurations substantially the same as the configurations described in connection with the above embodiments (e.g., a configuration having the same function, method, and results, or a configuration having the same objective and effects). The invention also includes a configuration in which an unsubstantial part (element) described in connection with the above embodiments is replaced by another part (element). The invention also includes a configuration having the same effects as those of the configurations described in connection with the above embodiments, or a configuration capable of achieving the same objective as that of the configurations described in connection with the above embodiments. The invention further includes a configuration in which a known technique is added to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. An electron spectrometer comprising:
   an energy analyzer section that energy-analyzes electrons emitted from a specimen;
   a micro-channel plate that amplifies the electrons analyzed by the energy analyzer section;
   a fluorescent screen that converts the electrons amplified by the micro-channel plate into light;
   a camera that photographs the fluorescent screen; and
   an effective range calculation section that calculates an effective range of the fluorescent screen within a camera image photographed by the camera,
   the effective range calculation section performing a process that acquires a plurality of the camera images photographed while causing the energy analyzer section to analyze the electrons with a different center energy, a process that converts the plurality of camera images respectively into a plurality of spectra, and a process that calculates the effective range of the fluorescent screen within the camera image based on the plurality of spectra.

2. The electron spectrometer as defined in claim 1, wherein, in the process that calculates the effective range of the fluorescent screen, the effective range calculation section determines a maximum brightness position within the camera image from each of the plurality of spectra, and then calculates the effective range of the fluorescent screen based on the center energy and the maximum brightness position.

3. The electron spectrometer as defined in claim 2, wherein, in the process that calculates the effective range of the fluorescent screen, the effective range calculation section draws a graph in which the center energy and the maximum brightness position are respectively plotted along a first axis and a second axis with respect to each of the plurality of spectra, and then calculates the effective range of the fluorescent screen from the graph.

4. The electron spectrometer as defined in claim 2, wherein the effective range calculation section performs a process that calculates an energy axis within the camera image based on the center energy and the maximum brightness position.

5. A measurement method that is implemented by an electron spectrometer that includes an energy analyzer section that energy-analyzes electrons emitted from a specimen, a micro-channel plate that amplifies the electrons analyzed by the energy analyzer section, a fluorescent screen that converts the electrons amplified by the micro-channel plate into light, and a camera that photographs the fluorescent screen, for calculating an effective range of the fluorescent screen within a camera image photographed by the camera, the measurement method comprising:
   a step that acquires a plurality of the camera images photographed while causing the energy analyzer section to analyze the electrons with a different center energy;
   a step that converts the plurality of camera images respectively into a plurality of spectra; and
   a step that calculates the effective range of the fluorescent screen within the camera image based on the plurality of spectra.

6. The measurement method as defined in claim 5, wherein the step that calculates the effective range of the fluorescent screen includes determining a maximum brightness position within the camera image from each of the plurality of spectra, and calculating the effective range of the fluorescent screen based on the center energy and the maximum brightness position.

7. The measurement method as defined in claim 6, wherein the step that calculates the effective range of the fluorescent screen includes drawing a graph in which the center energy and the maximum brightness position are respectively plotted along a first axis and a second axis with respect to each of the plurality of spectra, and calculating the effective range of the fluorescent screen from the graph.

8. The measurement method as defined in claim 6, further comprising:
   a step that calculates an energy axis within the camera image based on the center energy and the maximum brightness position.

* * * * *